United States Patent
Connell et al.

(10) Patent No.: US 6,469,031 B1
(45) Date of Patent: Oct. 22, 2002

(54) CARBOXYL SUBSTITUTED CHROMAN DERIVATIVES USEFUL AS BETA 3 ADRENORECEPTOR AGONISTS

(75) Inventors: Richard D. Connell, Trumbull, CT (US); Timothy G. Lease, El Cerrito, CA (US); Jeremy Baryza, New Haven, CT (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/216,512

(22) Filed: Dec. 18, 1998

(51) Int. Cl.$^7$ .................. A61K 31/44; C07D 405/00
(52) U.S. Cl. ..................... 514/337; 546/282.7
(58) Field of Search ............... 546/282.7; 514/337

(56) References Cited

U.S. PATENT DOCUMENTS

| | | | |
|---|---|---|---|
| 3,706,764 A | 12/1972 | Nakanishi et al. | 260/327 |
| 3,803,176 A | 4/1974 | Christensen et al. | 260/345.2 |
| 4,647,579 A | 3/1987 | Kabbe et al. | 514/456 |
| 4,650,812 A | 3/1987 | Cohen et al. | 514/456 |
| 4,654,362 A | 3/1987 | Van Lommen et al. | 514/452 |
| 5,137,901 A | * 8/1992 | Junge et al. | |
| 5,393,775 A | 2/1995 | Le Baut et al. | 514/456 |
| 5,451,677 A | 9/1995 | Fisher et al. | 546/138 |
| 5,516,917 A | 5/1996 | Djuric et al. | 548/525 |
| 5,541,197 A | 7/1996 | Fisher et al. | 514/311 |
| 5,561,142 A | 10/1996 | Fisher et al. | 514/312 |
| 5,663,194 A | 9/1997 | Newshaw | 514/456 |

FOREIGN PATENT DOCUMENTS

| | | | |
|---|---|---|---|
| DE | 2511647 | 9/1975 | ......... C07D/311/22 |
| EP | 0079637 | 5/1983 | ......... C07D/311/24 |
| EP | 0091749 | 10/1983 | ......... C07C/143/78 |
| EP | 0328251 | 8/1989 | ....... C07C/103/178 |
| EP | 0611003 | 8/1994 | ......... C07C/311/21 |
| EP | 0801060 | 10/1997 | ......... C07D/209/42 |
| FR | 2746395 | 9/1997 | ......... C07D/409/12 |
| JP | 08198866 | 8/1996 | |
| WO | 9429290 | 12/1994 | ......... C07D/307/85 |
| WO | 9525104 | 9/1995 | ......... C07D/405/12 |
| WO | 9529159 | 11/1995 | ......... C07D/213/30 |
| WO | 9735835 | 10/1997 | ......... C07C/217/74 |

* cited by examiner

*Primary Examiner*—Alan L. Rotman
*Assistant Examiner*—Binta Robinson

(57) ABSTRACT

This invention is related to novel carboxyl substituted chroman derivatives which are useful in the treatment of beta-3 receptor mediated conditions.

11 Claims, No Drawings

CARBOXYL SUBSTITUTED CHROMAN DERIVATIVES USEFUL AS BETA 3 ADRENORECEPTOR AGONISTS

FIELD OF THE INVENTION

This invention relates to novel chroman compounds, intermediates useful for their preparation, pharmaceutical compositions containing such compounds, and methods of selectively treating beta 3 adrenoreceptor mediated conditions with such compositions.

BACKGROUND OF THE INVENTION

Adrenoreceptors, or adrenergic receptors, are sites on effector organs that are innervated by postganglionic adrenergic fibers of the sympathetic nervous system, and are classified as alpha-adrenergic and beta-adrenergic receptors. Alpha-adrenergic receptors respond to norepinephrine and to such blocking agents as phenoxybenzamine and phentolamine, whereas beta-adrenergic receptors respond to epinephrine and to such blocking agents as propranolol.

Beta-adrenergic receptors are subclassified as beta-1, beta-2 and beta-3 adrenoreceptors. Beta-1 stimulation causes cardiostimulation, whereas beta-2 stimulation causes bronchodilation and vasodilation.

Beta-3 receptors are found on the cell surface of both white and brown adipocytes where their stimulation promotes both lipolysis and energy expenditure. Agonists selective for beta-3 adrenoreceptors are known to be useful in the treatment of hyperglycemia (diabetes) and obesity in mammals, as well as in the treatment of gastrointestinal disorders and neurogenetic inflammation (U.S. Pat. No. 5,561,142). Additionally, they are known to lower triglyceride and cholesterol levels and to raise high density lipoprotein levels in mammals (U.S. Pat. No. 5,451,677). Accordingly, they are useful in the treatment of conditions such as hyper-triglyceridaemia, hypercholesterolaemia and in lowering high density lipoprotein levels as well as in the treatment of atherosclerotic and cardiovascular diseases and related conditions.

Treatment of such chronic diseases with agonists that are selective for beta-3 adrenoreceptors decreases the potential for undesirable side effects caused by beta-1 or beta-2 receptor stimulation such as increased heart rate (beta-1) and muscle tremor (beta-2). It has now been found that certain novel chroman derivatives are effective as selective beta-3 agonists and are useful in the treatment of beta-3 mediated conditions.

DESCRIPTION OF THE INVENTION

This invention specifically relates to chroman compounds of formula I:

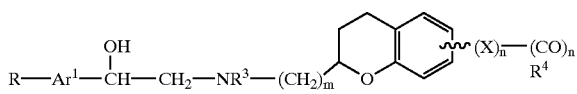

wherein:
R is hydrogen, hydroxy, oxo, halogen, $C_1-C_{10}$haloalkyl, $C_1-C_{10}$ alkyl, cyano, nitro, $NR^1R^1$, $SR^1$, $OR^1$, $SO_2R^2$, $OCOR^2$, $NR^1COR^2$, $COR^2$, $NR^1SO_2R^2$, $NR^1CO_2R^1$, $C_1-C_{10}$ alkyl, phenyl, pyrrole or a 5 or 6 membered heterocyclic ring with from 1 to 4 heteroatoms selected from O, S and N, each moiety being optionally substituted with hydroxy, halogen, cyano, $NR^1R^1$, $SR^1$, trifluoromethyl, $OR^1$, $C_3-C_8$ cycloaklyl, phenyl, $NR^1COR^2$, $COR^2$, $SO_2R^2$, $OCOR^2$, $NR^1SO_2R^2$, $NR^1CO_2R^1$, $C_1-C_{10}$ alkyl, $C_1-C_{10}$ alkoxy, and OR, and each ring moiety being optionally fused to a 5 membered heterocyclic ring containing from 1 to 4 hetero atoms selected from O, S, and N, the fused heterocyclic ring being optionally fused to a phenyl ring or optionally substituted with oxo;

R is hydrogen, $C_1-C_{10}$ alkyl optionally substituted with 1 to 4 substituents selected from hydroxy, halogen, $CO_2H$, $CO_2C_1-C_{10}$ alkyl, $SO_2C_1-C_{10}$ alkyl, $C_1-C_{10}$ alkoxy; or $C_3-C_8$ cycloalkyl, phenyl or naphthyl each optionally substituted with 1 to 4 substituents selected from halogen, nitro, oxo, $C_1-C_{10}$ alkyl, $C_1-C_{10}$ alkoxy, $C_1-C_{10}$ alkylthio;

$R^2$ is $R^1$ or $NR^1R^1$;

$R^3$ is hydrogen, $C_1-C_{10}$ alkyl, $CO_2R^1$, or

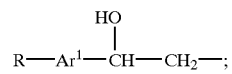

$Ar^1$ is phenyl, or a 5 or 6 membered heterocyclic ring with from 1 to 4 heteroatoms selected from O, S and N, each moiety being optionally fused to a 5 membered heterocyclic ring containing from 1 to 4 hetero atoms selected from O, S, and N, the fused heterocyclic ring being optionally fused to a phenyl ring or substituted with oxo;

m is 1, 2 or 3;

n is independently in each instance 0, 1 or 2;

X is $C_1-C_4$ alkyl optionally substituted with halogen;

$R^4$ is hydroxy, $C_1-C_{10}$ alkoxy, O—$R^1$ or $NR^1R^1$, and pharmaceutically acceptable salts and esters thereof.

The terms identified above have the following meaning throughout:

$C_1-C_4$ alkyl and $C_1-C_{10}$ alkyl each means straight or branched chain alkyl groups having from one to about four or from one to about ten carbon atoms respectively, which may be saturated, unsaturated or partially saturated Such groups include methyl, ethyl, n-propyl, isopropyl, n-butyl, isobutyl, sec-butyl, tert-butyl, as well as vinyl, allyl, propynyl, butenyl, butadienyl, isopropenyl, methyleneyl, ethylenyl, propyenyl, ethynyl, and the like.

$C_1-C_{10}$ haloalkyl means straight or branched chain alkyl groups having from about one to about ten carbon atoms, the alkyl groups being substituted with one or more halogen atoms, and includes such groups as trifluoromethyl, trichloromethyl, pentafluoroethyl, fluoromethyl, 6-chlorohexyl, and the like.

The term $C_1-C_{10}$ alkoxy means straight or branched chain alkoxy groups having from one to about ten carbon atoms and at least one oxygen atom where any C—C bond may be saturated or unsaturated, and includes such groups as methoxy, ethoxy, n-propoxy, isopropoxy, n-butoxy, isobutoxy, sec-butoxy, tert-butoxy, and the like.

$C_3-C_8$ cycloalkyl means saturated mono cyclic alkyl groups of from 3 to about 8 carbon atoms, and includes such groups as cyclopropyl, cyclopentyl, cyclohexyl, and the like.

$C_1-C_{10}$ alklthio means straight or branched chain thioalkyl groups having from one to about ten atoms selected from C and S and containing at least one or more S atoms, and includes such groups as thiomethyl, thioethyl, 2-thiopropyl, 2,4dithiohexyl, 8-methyl-2,4-dithiaethane, and the like.

Halogen includes fluorine, chlorine, bromine and iodine.

$Ar^1$ includes phenyl and such heterocyclic groups as pyridyl, quinolinyl, pyrimidinyl, pyrrolyl, thienyl, furanyl, imidazolyl, thiazolyl, benzimidazolyl, thiadiazolyl, benzothiadiazolyl, indolyl, indolinyl, benzodioxolyl, benzodioxanyl, benzothiophenyl, benzoxazinyl, benzisoxazolyl, benzothiazolyl, tetrahydronaphthyl, dihydrobenzofurnayl, tetrahydroquinolinly, fluropyridine, thienopyridine, 2-tetrazolo-[1,5a]pyridin-6-yl, benzofuranyl, carbazolyl, dibenzothiofuranyl, 2-tetrazolo-[1,5a]pyridin-6-yl, and the like.

$C_1$–$C_{10}$heteroalkyl means straight or branched chain saturated or unsaturated heteroalkyl groups having from one to about ten atoms selected from C, N, O, and S and containing at least one hetero atom, and includes such groups as ethers, amines, sulfides and the like.

When any moiety is described as being substituted, it can have one or more of the indicated substituents that can be located at any available position on the moiety. When there are two or more substituents on any moiety, each term shall be defined independently of any other in each occurrence. For example, $NR^1R^1$ may represent $NH_2$, $NHCH_3$, $N(CH_3)CH_2CH_2CH_3$, and the like.

The —$(X)_n$—$(CO)_n R_4$ side chain may be attached to the chroman moiety at any available position on the phenyl portion of the chroman moiety.

Illustrative examples of the compounds of this invention include the following compounds of Formula I:

2-{[2-(3-Chloro-phenyl)-2-hydroxy-ethylamino]-methyl}-chroman-6-carboxylic acid ethyl ester
{2-[(2-Hydroxy-2-pyridin-3-yl-ethylamino)-methyl]-chroman-6-yl}-acetic acid
3-{2-[(2-Hydroxy-2-pyridin-3-yl-ethylamino)-methyl]-chroman-6-yl}-propionic acid ethyl ester
3-{2-[(2-Hydroxy-2-pyridin-3-yl-ethylamino)-methyl]-chroman-6-yl}-propionic acid
2-{[2-(6-Amino-pyridin-3-yl)-2-hydroxy-ethylamino]-methyl}-chroman-6-carboxylic acid ethyl ester
2-{[2-(6-Amino-pyridin-3-yl)-2-hydroxy-ethylamino]-methyl}-chroman-6-carboxylic acid
(2-{[2-(6-Amino-pyridin-3-yl)-2-hydroxy-ethylamino]-methyl}-chroman-6-yl)-acetic acid ethyl ester
(2-{[2-(6-Amino-pyridin-3-yl)-2-hydroxy-ethylamino]-methyl}-chroman-6-yl)-acetic acid
3-(2-{[2-(6-Amino-pyridin-3-yl)-2-hydroxy-ethylamino]-methyl)-chroman-6-yl)-propionic acid ethyl ester
3-(2-{[2-(6-Amino-pyridin-3-yl)-2-hydroxy-ethylamino]-methyl}-chroman-6-yl)-propionic acid
2-{[2-(3-Chloro-phenyl)-2-hydroxy-ethylamino]-methyl}-chroman-6-carboxylic acid
(2-{[2-(3-Chloro-phenyl)-2-hydroxy-ethylamino]-methyl}-chroman-6-yl)-acetic acid ethyl ester
(2-{[2-(3-Chloro-phenyl)-2-hydroxy-ethylamino]-methyl}-chroman-6-yl)-acetic acid
3-(2-{[2-(3-Chloro-phenyl)-2-hydroxy-ethylamino]-methyl}-chroman-6-yl)-propionic acid ethyl ester
3-(2-{[2-(3-Chloro-phenyl)-2-hydroxy-ethylamino]-methyl}-chroman-6-yl)-propionic acid
2-[(2-Hydroxy-2-pyridin-3-yl-ethylamino)-methyl]-chroman-6-carboxylic acid ethyl ester
2-[(2-Hydroxy-2-pyridin-3-yl-ethylamino)-methyl]-chroman-6-carboxylic acid
{2-[(2-Hydroxy-2-pyridin-3-yl-ethylamino)-methyl]-chroman-6-yl}-acetic acid ethyl ester.
2-{[2-Hydroxy-2-(3-methoxy-phenyl)-ethylamino]-methyl}-chroman-6-carboxylic acid
2-[(2-Hydroxy-2-tetrazolo[1,5-a]pyridin-6-yl-ethylamino)-methyl]-chroman-6-carboxylic acid ethyl ester
4-(2-{[2-(4-Acetyl-phenyl)-2-hydroxy-ethylamino]-methyl}-chroman-6-yl)-N-methyl-2-{2-[(2-Hydroxy-2-pyrimidin-4-yl-ethylamino)-methyl]-chroman-6-yl}-acetamide
4-(2-{[2-(3-Cyano-phenyl)-2-hydroxy-ethylamino]-methyl}-chroman-8yl)-butyric acid pentyl ester
N-Ethyl-4-{2-[(2-hydroxy-2-pyrimidin-2-yl-ethylamino)-methyl]-chroman-6-yl}-N-methyl-butyramide
Ethyl(2E)-3-(2-{[((2R)-2-hydroxy-2-(3-pyridyl)ethyl)amino]methyl}(2S)chroman-6-yl)prop-2-enoate
(2E)-3-(2-({[(2R)-2-(6-amino(3-pyridyl))-2-hydroxyethyl]amino}methyl)(2S)chroman-6-yl]prop-2-enoic acid
(2Z)-3-(2{[((2R)-2-hydroxy-2-(3-pyridyl)ethyl)amino]methyl}(2S)chroman-6-yl)prop-2-enamide As is true of most classes of therapeutically effective compounds, certain subclasses and certain species which are especially effective are preferred over others. In this instance, those compounds of Formula I which are preferred include those compounds where $Ar^1$ is phenyl, pyridyl, or pyrimidinyl optionally substituted with halo, hydroxy, acetyl, cyano, alkyl or amino, $R^3$ is hydrogen, m is 1, n is 0 for the $(X)_n$ moiety, $(CO)_n R^4$ is $CO_2 R^1$ and is attached at the 6 position of the chroman moiety.

Representative salts of the compounds of Formula I include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconoate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, luaryl, myristyl and strearyl chlorides, bromides and iodides, aralkyl halides like benzyl and phenethyl bromides and others.

The esters in the present invention are non-toxic, pharmaceutically acceptable esters such as alkyl esters such as methyl, ethyl, propyl, isopropyl, butyl, isobutyl or pentyl esters. Additional esters such as phenyl-$C_1$–$C_5$ alkyl may be used, although methyl ester is preferred. The compound of Formula I may be esterified by a variety of conventional procedures including reacting the appropriate anhydride, carboxylic acid or acid chloride with the alcohol group of the Formula I compound. The appropriate anhydride is reacted with the alcohol in the presence of an acylation catalyst such as 1,8-bis[dimethylamino]napthalene or N,N-dimethylaminopyridine. An appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be reached using the appropriate carboxylic acid in the presence of trifluoroacetic anhydride and, optionally, pyridine, or in the presence of N,N-carbonyldiimidazole with pyridine. Reaction of an acid chloride with the alcohol is carried out with an acylation catalyst such as 4-DMAP or pyridine.

Sensitive or reactive groups on the compound of Formula I may need to be protected during any of the above methods for forming esters, and protecting groups may be added and removed by conventional methods well known in the art.

One skilled in the art would readily know how to successfully carry out these as well as other methods of esterification of alcohols.

The compounds of this invention may, either by nature of asymmetric centers or by restricted rotation, be present in the form of isomers. All isomers, whether separated, pure, partially pure or in racemic mixture, of the compounds of this invention are encompassed within the scope of this invention. The compounds of Formula I wherein the hydroxy component on the $Ar^1$ side chain is in the Rectus configuration (above the plane as depicted in Formula I) is preferred. The purification of said isomers and the separation of said isomeric mixtures can be accomplished by standard techniques known in the art.

The particular process to be utilized in the preparation of the compounds of this invention depends upon the specific compound desired. Such factors as the selection of the specific $Ar^1$, X and $(CO)_nR^4$ moieties, and the specific substituents on the various moieties, all play a role in the path to be followed in the preparation of the specific compounds of this invention. Those factors are readily recognized by one of ordinary skill in the art.

The compounds of Formula I of the present invention can be prepared as indicated in the following Reaction Schemes.

In general, the compounds of this invention may be prepared by standard techniques known in the art and by known processes analogous thereto. The compounds of Formula I can generally be synthesized according to Reaction Scheme 1 wherein the appropriate epoxide 1 is coupled with the appropriate amine 2. This reaction is typically carried out in an aprotic solvent such as dimethyl sulfoxide, dimethyl formamide, acetonitrile, or in an alcohol such as ethanol, isopropanol or propanol at temperature from about −10° C. to reflux. Compounds of formula I wherein $R^4$ is an alkoxy, can be further converted to the corresponding carboxylic acid form by standard hydrolysis procedures known to one skilled in the art.

REACTION SCHEME 1

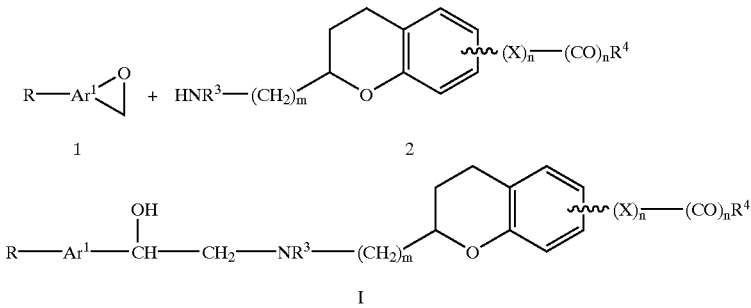

For synthesis of any particular compound, one skilled in the art will recognize that the use of protecting groups may be required for the synthesis of compounds containing certain substituents. A description of suitable protecting groups and appropriate methods of removing such groups may be found in: *Protective Groups in Organic Synthesis*, Second Edition, T. W. Greene, John Wiley and Sons, New York, 1991. For example, after preparation of a compound according to Reaction Scheme 1, in order to enable purification of the end product by, for instance, flash chromatography, compounds of Formula I wherein $R^3$ is, for example, H, can be selectively protected as, for example, a carbamate derivative obtained by, for example, treatment with a reagent such as di-tert-butyl dicarbonate or other means known in the art. After purification, the carbamate group can easily be removed by treatment with an acid such as HCl or trifluoroacetic acid by means known in the art.

The epoxide 1 of Reaction Scheme 1 is commercially available or may be prepared according to one of the many procedures described in the literature known to those skilled in the art. A representative synthesis of epoxide 1 is outlined in Reaction Scheme 2. Arylketone 3 can be halogenated with a reagent such as N-chlorosuccinimide (NCS) in a protic solvent such as acetic acid/hydrochloric acid mixture (HCl) to afford the chloroacetyl 4. Treatment of 4 by a reducing agent such as sodium borohydride ($NaBH_4$) in a polar solvent such as methanol (MeOH), gives the corresponding alcohol 5. The epoxide 1a can be obtained by treating alcohol 5 with a base such as potassium carbonate ($K_2CO_3$) in a solvent such as acetone.

In this particular synthesis, compounds 5 and 1a are both racemic and the pure enantiomeric form of each compound can be obtained by chiral chromatography. It may be appreciated by one skilled in the art that there are several methods which can produce enantiomerically enriched (R) or (S) epoxide 1a by asymmetric reduction of the haloketone 4. Asymmetric reduction can be accomplished using chiral reducing agents such as, but not limited to, (−) or (+)-DIP-Cl and (R) or (S)-Alpine borane.

REACTION SCHEME 2

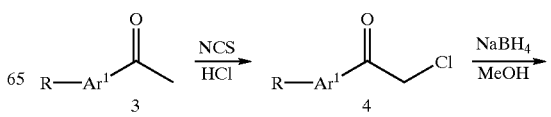

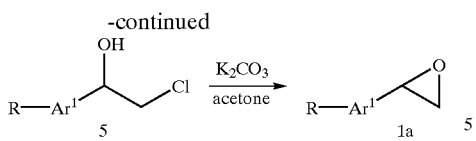

An alternative synthesis of epoxide 1 wherein $Ar^1$ is a pyridine ring fused to a 5 membered heterocyclic ring containing 4 nitrogen atoms (1b) is outlined in Reaction Scheme 3. Chlorinated 3-acetyl-pyridine 7 can be obtained from treating the acyl chloride 6 with dimethylmalonate, a reagent such as magnesuim chloride and a base such as triethylamine ($CH(CO_2Me)_2$, $Et_3N$, $MgCl_2$). The intermediate can undergo a decarboxylation at high temperature in a polar solvent such as dimethylsulfoxide (DMSO), according to a procedure described by Kuo (*Tetahedron,* 1992, 48, 9233). Treatment of 7 with sodium azide ($NaN_3$) in a polar solvent such as methanol in the presence of an acid such as hydrochloric acid (HCl), affords the corresponding tetrazolopyridine 8. The ketone 8 can be brominated with a reagent such as N-bromosuccinimide (NBS) in a protic solvent such as acetic acid/HBr mixture (AcOH/HBr) to afford the bromoacetyl 9. Treatment of 9 by a reducing agent such as sodium borohydride ($NaBH_4$) in a polar solvent such as methanol, followed by an in situ treatment with a base such as sodium hydroxide (NaOH) affords the epoxide 1b.

By analogy to the synthesis of epoxide 1a, epoxide 1b can be obtained in its pure enantiomeric form by asymmetric reduction of the haloketone 9, using the chiral reagents previously described.

The epoxide 1b may be used according to Reaction Scheme 1 to produce the compound of Formula I wherein $Ar^1$ is a pyridine ring fused to a 5 membered heterocyclic ring containing 4 nitrogen atoms, and may be further treated by methods known in the art to cleave the fused heterocyclic ring from the 6 membered ring, resulting in the compounds of Formula I wherein $Ar^1$ is pyridine substituted with $NH_2$.

REACTION SCHEME 3

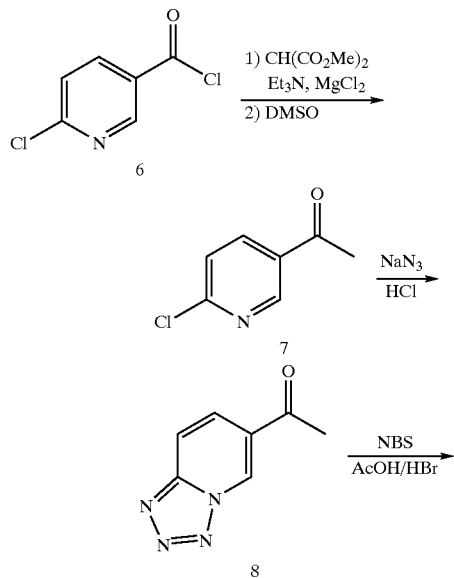

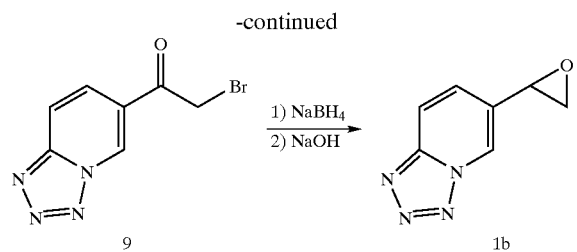

A representative synthesis of the amine 2 wherein the n in $(X)_n$ is 0 and $(CO)_nR^4$ is $CO_2R^1$ (2a) is outlined in Scheme 4. The hydroxyacetophenone 10 (commercially available) is treated with diethyl oxalate in the presence of a base such as sodium ethoxide in a polar solvent such as ethanol. After work-up, the residue can be treated with a mixture of acetic acid and hydrochloric acid, to afford the carboxylic acid 11. Hydrogenation of 11 using a catalyst such as palladium on activated carbon, gives the chroman 12. The chroman-carboxylic acid 12 can be treated with dichloromethyl methyl ether and aluminum chloride to give the formyl-chroman 13 mainly substituted at the position 6. Other methods known to one skilled in the art may allow a different substitution pattern, for example, the starting material (hydroxyacetophenone 10) could be substituted at any of the aromatic positions by a functional group that can later be transformed to other regioisomers of the formyl-chroman 13, using the same or similar reaction sequence. The formyl-chroman 13 can be successively treated with reagents such as oxalyl chloride and ammonia to afford the formyl-chroman-amide 14. The formyl-chroman-amide 14 can be treated with a reagent such as trifluoroacetic anhydride in an inert solvent such as tetrahydrofuran with a base such as triethylamine to afford the formyl-chroman-nitrile 15. The formyl-chroman-nitrile 15 can be treated with chemical oxidizing agents such as sodium chlorite in a buffer solution, followed by an esterification procedure using an alkyl halide such as ethyl iodide with a base such as 1,8-diazabicyclo [5.4.0]undec-7-ene to give the ester-chroman-nitrile 16. Compound 16 can be treated with hydrogen in the presence of a metal catalyst, such as palladium on carbon, in a polar solvent such as ethanol, to give the primary amine 2a.

REACTION SCHEME 4

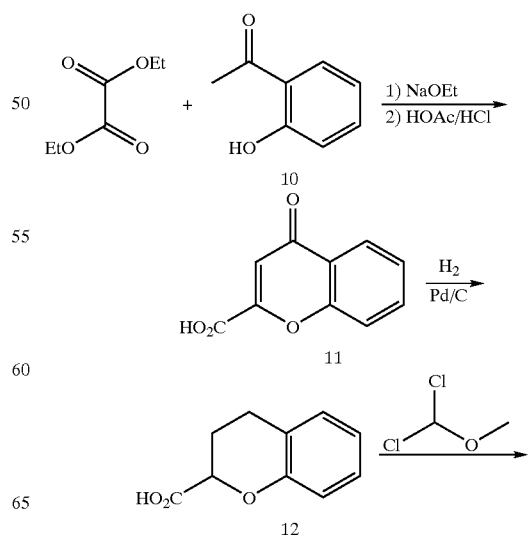

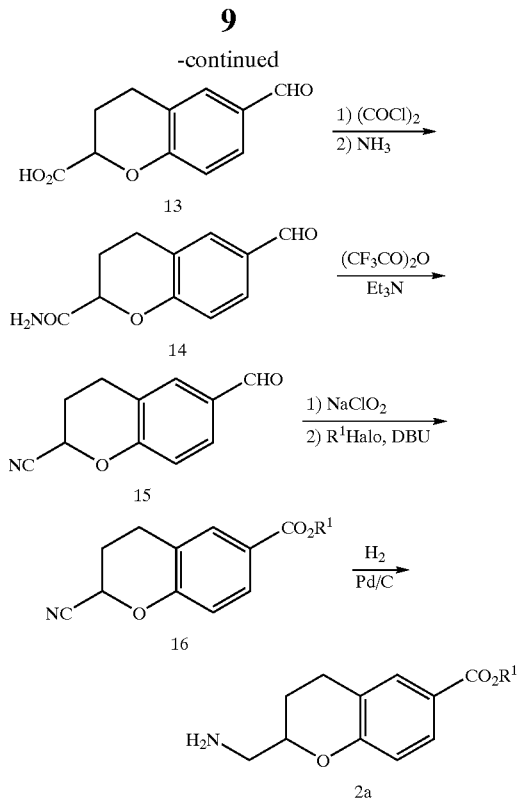

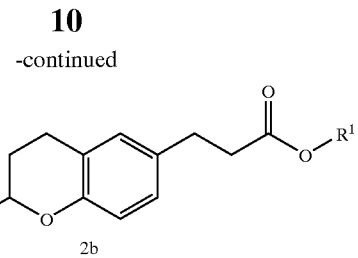

Compounds of formula 2 wherein $(CO)_nR^4$ are other than $CO_2R^1$ can be made by methods known to those skilled in the art. For example, ester 2a or 16 can be saponified to the corresponding carboxylic acid by using a base such as sodium hydroxide in a polar solvent such as methanol. The carboxylic acid can then be successively treated with reagents such as oxalyl chloride and an amine to afford the corresponding amide as illustrated in Scheme 4.

A representative synthesis of the amine 2 wherein the n in $(X)_n$ is 2 and $(CO)_nR^4$ is $CO_2R^1$ (2b) is outlined in Scheme 5. Wittig reaction with compound 15 and an ylide such as 17, in an inert solvent such as tetrahydrofuran can afford the olefin 18. Compound 18 can be treated with hydrogen in the presence of a metal catalyst, such as palladium on carbon, in a polar solvent such as ethanol, to give the primary amine 2b.

REACTION SCHEME 5

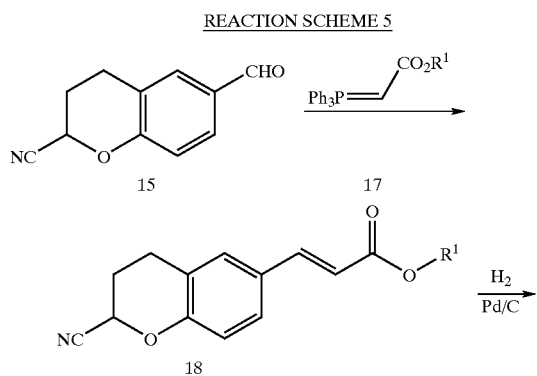

Compound 2 of Reaction Scheme 1 wherein m is other than 1 can be synthesized from derivatives of compound 12. For example, compound 12 can be reduced to the corresponding alcohol by treatment with a reducing agent such as lithium aluminum hydride. The resulting alcohol can then be oxidized to the corresponding aldehyde by treatment with an oxidizing reagent such as PCC (pyridinium chlorochromate) in an appropriate solvent. The resulting aldehyde can undergo an alkyl chain extension according to well known procedures such as that described by Wittig, G. et al., in *Chem.Ber.*, 1962, 2514. This aldehyde with the extended alkyl chain can be converted to a carboxyclic acid by standard methods of oxidation well known by those skilled in the art, and can be used in place of compound 12 to make compound 2 of Reaction Scheme 1 by analogy to compound 12 in Reaction Schemes 4 and 5.

Another representative synthesis of amine 2 where the n in $(X)_n$ is 0 and $(CO)_nR^4$ is $CO_2R^1$ (2a) is outlined in Scheme 6. Compound 12 can be treated with an haloganating agent such as benzyltrimethylammonium dichloroiodate in the presence of a catalyst such as zinc chloride in a polar solvent such as acetic acid to give the corresponding iodoaryl 19. Compound 19 can undergo carbonylation with reagents such as carbon monoxyde and an alcohol such as methanol, in the presence of a catalyst such as paladium acetate and a base such as triethylamine to give ester 20. Compound 20 can be transformed to the corresponding cyano 16 by treatment with an acylating agent such as oxalyl chloride in a solvent such as tetrahydrofuran, followed by a successive treatment with ammonia then triflic anhydride in the presence of a base such as triethylamine (Chem. Com. 1998, 259). Compound 16 can be transformed to amine 2a according to the step described in Reaction Scheme 4.

REACTION SCHEME 6

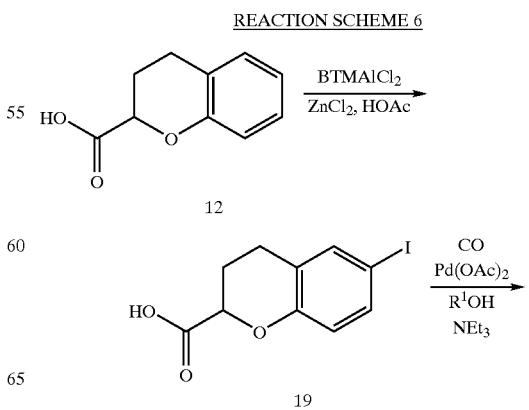

-continued

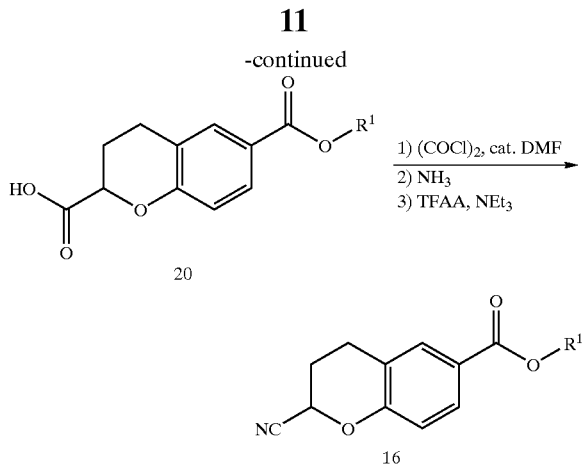

A variation of Reaction Scheme 6 which can produce amine of type 2 where the n in $(X)_n$ is 2 and $(CO)_n R^4$ is $CO_2 R^1$ is outlined in Reaction Scheme 7. Compound 19 is treated similarly as in Reaction Scheme 6, but with a different alkylating agent such as methyl acrylate to give ester 21. Compound 21 can be treated by a reducing agent such as sodium borohydride in the presence of a catalyst such as copper chloride in a solvent such as methanol or ethanol to give ester 22. Compounds 21 and 22 can be further transformed to amine of type 2 according to the steps described in Schemes 6 and 4.

REACTION SCHEME 7

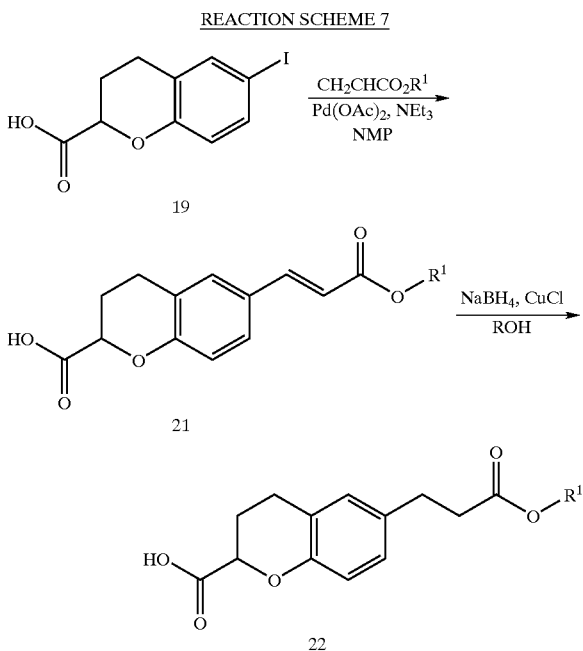

Compound 21 can also be optionally transformed to make compounds wherein X is optionally halogenated by procedures such as addition of a halogen such as bromine, chlorine, iodine chloride or the like, to the olefin moiety by methods known by those skilled in the art.

The foregoing reaction schemes are further illustrated by the specific Examples described later herein.

The salts and esters of this invention can be readily prepared by conventional chemical processes.

The compounds of Formula I of this invention are preferably selective beta-3 adrenergic receptor agonists that effect beta-3 adrenergic receptor mediated conditions without concurrent beta-1 and/or beta-2 receptor mediated side effects. Accordingly, an embodiment of the present invention is the administration of the compounds of this invention to a human or animal for the treatment of beta-3 receptor mediated conditions such as diabetes, obesity, gastrointestinal disorders including irritable bowel syndrome and intestinal hypermotility disorders, peptic ulcerations, esophagitis, gastritis, and duodenitis, intestinal ulcerations including inflammatory bowel disease, ulcerative colitis, Crohn's disease and proctitis, and gastrointestinal ulcerations, as well as neurogenetic inflammation such as cough and asthma, and depression. It is also believed that the compounds of this invention are effective in the treatment of hypertriglyceridaemia, hypercholesterolaemia and conditions of low or high density lipoprotein levels, artheroscierotic disease and cardivacular disease and related conditions. Additionally, it is also believed that the compounds of this invention are effective in the treatment of ocular hypertension and glaucoma, as platelet aggregation inhibitors, and in the treatment of urinary disorders including pollakiuria and incontinence, as well as in the treatment of prostate diease and as topical anti-inflammatory agents.

Therefore, the compounds of this invention are expected to be valuable as therapeutic agents. An embodiment of this invention includes a method of treating beta-3 adrenergic receptor mediated conditions in a mammal which comprises administering to said mammal a composition containing an amount of the compound of Formula I that is effective in treating the target condition.

The specificity of the compounds of this invention as beta-3 adrenergic receptor agonists can readily be determined by evaluating the affinity of the compound for the different beta adrenergic receptor subtypes and comparing the activity with various receptor subtypes affinities to discover specificity as well as activity. This can be determined by standard and well-known procedures. For example, the utility of the present invention as beta-3 adrenergic receptor agonists useful in treating beta-3 adrenergic receptor mediated conditions can be demonstrated by the following procedure.

Chinese hamster ovary (CHO) cells that stably express full-length human beta-3-adrenergic receptor (Emorine, L. J. et al: *Molecular Characterization of the Human Beta-3-Adrenergic Receptor*. Science (Wash. DC) 245: 1118–1121, 1989) were used in the following procedure. All cell lines were grown in 90% F12 nutrient mixture (HAM), 10% fetal bovine serum, 100 units/ml penicillin G sodium, 100 mg/ml streptomycin sulfate and 2 mM L-glutamine at 37° C. in 95% air and 5% $CO_2$. The transfected cell lines are exposed to G-418 (800 ug/ml) every $4^{th}$ passage or so.

To test the agonist activity, cells are exposed to test compound and then assayed for cAMP production. 100 ul CHO cells are plated at $5 \times 10^4$ cells/well of a 96 well plate (#3596, Costar, Cambridge, Mass.) to achieve 70% confluency the next day. After overnight incubation at 37° C. media is removed and the cells are treated for 30 minutes at 37° C. with KRP buffer(120 mM NaCl, 5.1 mM KCl, 0.6 mM $MgSO_4.7H_2O$, 0.8 mM $CaCl_2.H_2O$, 12.5 uM Phosphate buffer, 20 uM Hepes pH 7.4)+0.2 uM IBMX (100 ul/well), +1% DMSO, +/− test compounds (10 uM DMSO stocks). Test compounds are assayed from 10 uM to 3 nM with 3 fold serial dilutions. The control compound, isoproterenol (10 mM stock in 1.1 mM ascorbate), is a general agonist of all three adrenergic receptors and is assayed by 3 fold dilution beginning at 1 uM. All test compound activities are expressed as % of the maximal response of 1 uM isoproterenol. The expected $EC_{50}$ values of isoproterenol for the beta-3, beta-2, and beta-1 receptors are 5 nM, 1 nM and 0.2 nM, respectively.

After the 30 minute incubation with the test compounds, the buffer/compound mixture is removed and the cells are treated with 200 ul per well 65% ethanol for 10 minutes at room temperature. 150 ul per well of this lysate is then transferred to a Scintillation Proximity Assay plate (#6005162, Packard, Meriden, Conn.) and the plate is dried at 37° C. for 1.5 hours.

The cAMP SPA screening assay system (#RPA 556, Amersham, Arlington Heights, Ill.) is used to measure the amount of cAMP produced.

In tests utilizing the above described procedures, the test compounds of the present invention were found to have beta-3 adrenergic agonist activity, preferably, selective beta-3 adrenergic agonist activity.

Based upon the above and other standard laboratory techniques known to evaluate compound receptor site inhibition, by standard toxicity tests and by standard pharmacological assays for the determination of treatment of the beta-3 receptor mediated conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.01 mg/kg to about 100 mg/kg, and preferably from about 0.1 mg/kg to about 20 mg/kg body weight per day. A unit dosage may contain from about 5 mg to about 1500 mg of active ingredient, and can be administered one or more times per day. Of course the specific initial and continuing dosage regimen for each patient will vary according to the nature and severity of the condition as determined by the attending diagnostician.

The compounds of this invention can be utilized to achieve the desired pharmacological effect by administration to a patient in need thereof in an appropriately formulated pharmaceutical composition. A patient, for the purpose of this invention, is a mammal, including a human, in need of treatment for a particular beta-3 adrenergic receptor mediated condition or disease. Therefore, the present invention includes pharmaceutical compositions which are comprised of a pharmaceutically acceptable carrier and a pharmaceutically effective amount of a compound of Formula I, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compounds of Formula I can be administered with a pharmaceutically-acceptable carrier using any effective conventional dosage unit forms, including immediate and timed release preparations, orally, parenterally, topically, or the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, cornstarch or gelatin, disintegrating agents intended to assist the break-up and dissolution of the tablet following administration such as potato starch, alginic acid, corn starch, and guar gum, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent or emulsifying agent.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative and flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane4-methanol, ethers such as poly (ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (See, e.g., U.S. Pat. No. 5,023,252, issued Jun. 11, 1991, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

The compound of this invention can be administered as the sole pharmaceutical agent or in combination with one or more other pharmaceutical agents where the combination causes no unacceptable adverse effects. For example, the compounds of this invention can be combined with known anti obesity or other indication agents, and the like, as well as with admixtures and combinations thereof.

The compounds of Formula 1 may also be utilized, in free base form or in compositions, in research and diagnostics, or as analytical references standards, and the like. Therefore, the present invention includes compositions which are comprised of an inert carrier and an effective amount of a compound of Formula I, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

The following specific examples are presented to illustrate the inventions described herein, but they should not be construed as limiting the scope of these inventions in any way.

The novel compounds useful in the therapeutic method of this invention are prepared by conventional methods of organic chemistry. Unless otherwise noted, reagents and solvents were obtained from commercial suppliers and were used without further purification.

Melting points were recorded in open capillary tubes and are uncorrected.

$^1$H NMR spectra were determined at 300 MHz using a General Electric GE-OMEGA 300 spectrometer. Chemical shifts are reported in parts per million (δ) values relative to tetramethylsilane as internal standard. Spin multiplicities are reported using the following abbreviations: singlet (s), doublet (d), triplet (t), quartet (q), multiplet (m), and broad (br). Coupling constants are in Hertz.

Fast atom bombardment (FAB) mass spectra were recorded using a Kratos Concept 1 spectrometer; electron impact (EI) and chemical ionization (CI) mass spectra were recorded using a Hewlett-Packard MS Engine (HP5989A) spectrometer; liquid chromatography-mass spectra (LC-MS) were recorded using a Finningan MAT LCQ spectrometer. Unless otherwise specified, mass spectra were obtained using the FAB method.

TLC was performed on silica gel plates using the following solvent systems: (A) 50:50 hexane/ethyl acetate; (B) 33:67 hexane/ethyl acetate; (C) ethyl acetate; (D) 45:45:10 hexane/ethyl acetate/methanol; (E) tetrahydrofuran (THF).

EXAMPLE 1

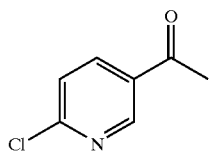

5-Acetyl-2-chloropyridine

Triethylamine (19 mL, 0.14 mol) and dimethyl malonate (7.8 mL, 59 mmol) were added to a round bottom flask containing magnesium chloride (3.8 g, 40 mmol) in anhydrous toluene (46 mL). The mixture was stirred at 25° C. for 1 h. A solution of 6-chloronicotinyl chloride (10 g, 57 mmol) in anhydrous toluene (50 mL) was slowly added to the mixture. The reaction was stirred for 1 h, then concentrated HCl (16 mL) was slowly added to the reaction. Diethyl ether (300 mL) was added and the organic layer was washed with water (2×100 mL). The organic layer was dried (MgSO$_4$), filtered, and concentrated to afford an oil. The product was stirred in hexanes (200 mL), eventually forming an off-white powder (12.7 g). The powder was treated with DMSO (31 mL) and water (1 mL). The reaction was stirred and heated to 165° C. for 2 h. The reaction was cooled to room temperature, diluted with diethyl ether (250 mL), and washed with water (4×200 mL). The organic layer was dried (MgSO$_4$), filtered, and concentrated to afford a white solid. The product was passed through a pad of silica (5% diethyl ether/hexane) to yield a white solid (6.0 g, 68%). R$_f$=0.2 (CH$_2$Cl$_2$); mp 100–102° C.; $^1$H NMR (300 MHz, CDCl$_3$) δ8.94 (s, 1H), 8.20 (dd, J=6, 9 Hz, 1H), 7.44 (d, J=8 Hz, 1H), 2.63 (s, 3H); MS (EI) m/z 155 (M$^+$).

EXAMPLE 2

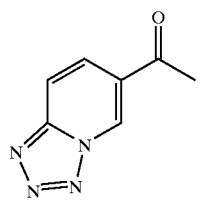

6-Acetyl tetrazol[1,5-α]pyridine

A solution of 5-acetyl-2-chloropyridine (500 mg, 3.2 mmol) in ethanol (8 mL) and water (3 mL) was carefully treated with sodium azide (0.42 g, 6.4 mmol). Concentrated HCl (0.4 mL) was added dropwise at room temperature. The reaction was refluxed for 16 h and then cooled to room temperature. Saturated NaHCO$_3$ was added dropwise until the pH=7. Dichloromethane (100 mL) was added and the reaction was washed with water (2×100 mL). The organic layer was dried (MgSO$_4$), filtered, and concentrated to afford a white solid (390 mg, 75%). R$_f$=0.1 (CH$_2$Cl$_2$); mp 156–158° C.; $^1$H NMR (300 MHz, CDCl$_3$) δ9.44 (s, 1H), 8.23 (dd, J=8, 10 Hz, 1H), 8.09 (dd, J=9, 10 Hz, 1H), 2.75 (s, 3H); MS (EI) m/z 162 (M$^+$).

EXAMPLE 3

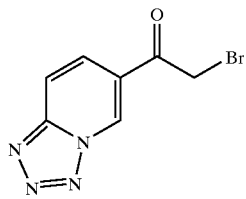

6-Bromoacetyltetrazolo[1,5-a]pyridine

6-Acetyl tetrazolo[1,5-a]pyridine (10 g, 62 mmol) in of acetic acid (160 mL) was treated with 30% HBr in acetic acid (14.7 mL, 247 mmol) at 0° C. N-bromosuccimide (11 g, 62 mmol) was slowly added and the reaction stirred for 30 minutes. Another 4 equivalents of 30% HBr in acetic acid (14.7 mL, 247 mmol) was slowly added and the reaction was allowed to warm to room temperature. After 3 hours, the reaction was diluted with ethyl acetate (500 mL) and washed with water (3×300 mL). The organic layer was dried (MgSO$_4$), filtered, and concentrated to afford an oil. Hexanes (75 mL) and dichloromethane (10 mL) were added to the oil and re-concentrated to afford a yellow solid (12.8 g, 86%). R$_f$=0.2 (CH$_2$Cl$_2$); mp 108–110° C.; $^1$H NMR (300 MHz, CDC$_3$) δ10.2 (s, 1H), 8.29 (dd, J=9, 10 Hz, 1H), 8.18 (dd, J=8, 10 Hz, 1H), 5.06 (s, 2H); MS (cz) m/z 241 (MH$^+$).

EXAMPLE 4

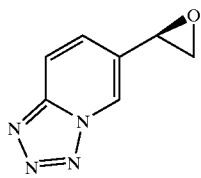

(R)-2-(tetrazolo[1,5-a]pyrid-6-yl)oxirane

6-Bromoacetyltetrazolo[1,5-a]pyridine (55 g, 0.23 mol) was added ethanol (400 mL) and slowly treated with sodium borohydride (17 g, 0.46 mol) at 0° C. The reaction was allowed to warm to room temperature for 1 h. Ethyl acetate (400 mL) and 1N NaOH (400 mL) was added to the reaction. The organic layer was separated, washed with water, dried (MgSO$_4$), filtered and concentrated to leave an oily residue. Flash chromatography (10% acetonitrile in hexane) yielded an off-white solid (17 g, 46%). The racemate was separated using a Diacel Chiralpak AS column (100% MeOH, 1.0 mL/min.) yielding the (R)-2-(tetrazolo[1,5-a]pyrid-6-yl) oxirane (7 g) in 99% ee. R$_f$=0.16 (CH$_2$Cl$_2$); mp 106–8° C.; $^1$H NMR (300 MHz, CDCl$_3$) δ9.38 (s, 1H), 8.17 (d, J=9, Hz, 1 H), 8.17 (dd, J=8, 10 Hz, 1H), 4.16 (m, 1H), 3.22 (m, 1H), 3.09 (m, 1H); MS (EI) m/z 162 (M$^+$); [α]$^{22}$=+6.0.

EXAMPLE 5

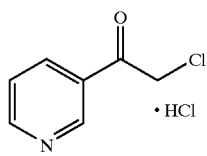

3-(2-Chloroacetyl)pyridine hydrochloride

To a solution of 3-acetylpyridine (100 g, 0.83 moles) in diethyl ether (1 L) was added of 1 N hydrogen chloride in ether (950 mL) with rapid stirring. The precipitated solids were filtered, washed with ether and dried. The hydrochloride salt (129 g, 0.83 mol) was added to a 5 L reactor equipped with a mechanical stirrer and dissolved with 1 N HCl in acetic acid (830 mL). The mixture was stirred until a clear solution was obtained, then N-chlorosuccinimide (111 g, 0.83 mol) was added, resulting in a yellow mixture. The solution was stirred at room temperature for 18 hours, gradually becoming a colorless suspension. The solids were collected by filtration and washed with ether; the filtrate was treated overnight with N-chlorosuccinimide (80 g, 0.6 mole) and additional product was collected to yield a white solid (152 g, 95%). $^1$H-NMR (300 MHz, DMSO-d$_6$) δ10.3 (br s, 1H), 9.27 (s, 1H), 8.96 (d, 1H, J=5.1 Hz), 8.62 (d, 1H, J=9.9 Hz), 7.89 (m, 1H), 5.30 (s, 2H); MS (EI) m/z 155 (M$^+$).

EXAMPLE 6

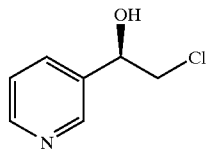

(R)-Chloromethyl-3-pyridinemethanol

A stirred, cold (−10° C.) suspension of 3-(2-chloroacetyl) pyridine hydrochloride (250 g, 1.6 mole) in methanol (1.5 L) was carefully treated with sodium borohydride (74 g, 1.95 mole) over a period of 1 hour. The resulting yellow suspension was stirred for an additional 40 minutes and was quenched by the addition of water (500 mL). The mixture was then concentrated in vacuo to remove methanol, diluted with water and neutralized with acetic acid. The biphasic mixture was extracted with ethyl acetate, dried (Na$_2$SO$_4$), filtered and concentrated in vacuo. The crude racemic mixture was purified by silica gel chromatography (ethyl acetate/hexane) to give 146.5 g of a yellow oil which was then resolved by chiral chromatography to afford the pure enantiomer as a dark orange oil, 75 g (containing residual solvent). $^1$H-NMR (300 MHz, CDCl$_3$) δ8.58 (s, 1H), 8.53 (d, 1H, J=4.8 Hz), 7.78 (d, 1H, J=7.9 Hz), 7.32 (m, 1H), 4.96 (m, 1H), 3.71 (m, 1H); MS

EXAMPLE 7

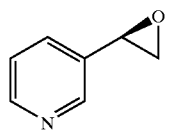

(R)-(Pyrid-3-yl)oxirane

To a solution of (R)-chloromethyl-3-pyridinemethanol (74 g, 0.47 moles) in acetone (2 L) was added potassium carbonate (300 g, 2.2 moles). The stirred mixture was heated to reflux for 18 hours and then cooled to room temperature. The dark red suspension was filtered and the filtrate was concentrated to dryness in vacuo . Flash chromatography (silica gel, 0–5% methanol/dichloromethane) afforded (26 g, 46%) of an orange oil. $^1$H-NMR (300 MHz, CDCl$_3$) δ8.56 (m, 2H), 7.53 (d, 1H, J=7.7 Hz), 7.28 (m, 1H), 3.88 (m, 1H), 3.18 (t, 1H, J=4.8 Hz), 2.81 (m, 1H); MS (EI) m/z 121 (M$^+$).

EXAMPLE 8

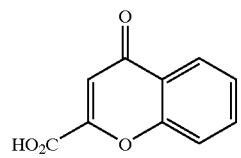

4-Oxo4H-chromene-2-carboxylic acid

A mixture of diethyl oxalate (110 mL, 810 mmol) and 2'-hydroxyacetophenone (44 mL, 365 mmol) was added over 20 minutes to a solution of sodium ethoxide (76 g, 1.11 mol) in ethanol (600 mL). The mixture was heated to 80° C.

for one hour then cooled to room temperature. Water (500 mL) and diethyl ether (600 mL) were added, and the mixture acidified to pH=2 with concentrated HCl. The organic phase was separated and the aqueous phase further extracted with diethyl ether (2×). The combined organic phase was washed with saturated aqueous sodium chloride solution (2×), dried (MgSO$_4$), and concentrated to give an oily brown solid.

The solid was mixed with glacial acetic acid (440 mL) and concentrated HCl (110 mL) and heated to 85° C. overnight. The mixture was cooled to room temperature, diluted with water (550 mL), and filtered. The solids were washed with water (2×125 mL) and dried in a vacuum oven to give a purple solid (58 g, 83%). Mp 260–261° C.; $^1$H NMR (300 MHz, DMSO-d$_6$) δ8.03 (m, 1H), 7.85 (m, 1H), 7.71 (m, 1H), 7.51 (m, 1H), 6.89 (s, 1H).

EXAMPLE 9

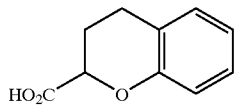

(±)-Chroman-2-carboxylic acid

A mixture of the compound from Example 8 (20.0 g, 105 mmol), and 10% palladium on activated carbon (2.0 g) in acetic acid (200 mL) was placed under hydrogen pressure (60 psig) in a Parr hydrogenation apparatus. After 22.5 hours the mixture was removed from the hydrogen atmosphere and filtered through a pad of Celite. The Celite pad was washed with ethyl acetate (800 mL), and the combined filtrate concentrated to give a brown oil. The oil was dissolved in ethyl acetate (500 mL) and extracted with saturated NaHCO$_3$ (4×125 mL). The aqueous phase was acidified to pH=2 with concentrated HCl and extracted with ethyl acetate (4×100 mL). The combined organic phase was washed with saturated aqueous sodium chloride solution (100 mL), and dried (MgSO$_4$), and concentrated to give a colorless solid (18.0 g, 96%). Mp 97.5–99° C.; $^1$H NMR (300 MHz, DMSO-d$_6$) δ12.96 (br s, 1H), 7.03 (m, 2H), 6.78 (m, 2H), 4.74 (dd, J=6.4 Hz, J=3.9 Hz, 1H), 2.73 (m, 1H), 2.63 (m, 1H), 2.03 (m, 2H).

EXAMPLE 10

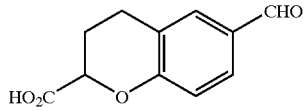

(±)-6-Formyl-chroman-2-carboxylic acid

A solution of the compound from Example 9 (11.5 g, 64.5 mmol) in dichloromethane (60 mL) was added to a cooled (−10° C.) mixture of aluminum chloride (21.5 g, 161 mmol) in dichloromethane (30 mL). The mixture was cooled to −30° C. for 20 minutes and dichloromethyl methyl ether (11.7 mL, 129 mmol) was added dropwise over one hour. After an additional 45 minutes the mixture was poured into a mixture of ice (325 mL) and concentrated HCl (5 mL). The mixture was filtered and the filtrate removed. The collected solids were dissolved in tetrahydrofuran. The tetrahydrofuran solution was dried (MgSO$_4$) and concentrated to give a solid. The solid was washed with dichloromethane (3×25 mL) and dried in vacuo at room temperature to give a light pink solid (4.34 g, 33%). $^1$H NMR (300 MHz, DMSO-d$_6$) δ13.17 (br s, 1H), 9.81 (s, 1H), 7.64 (m, 2H), 6.99 (d, J=9.2 Hz, 1H), 4.94 (t, J=5.0 Hz, 1H), 2.87 (m, 1H), 2.68 (m, 1H), 2.14 (m, 2H); MS (FAB) m/z 207 (MH$^+$).

EXAMPLE 11

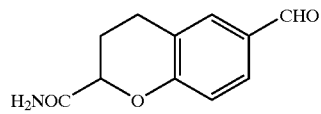

(±)-6-Formyl-chroman-2-carboxylic acid amide

Oxalyl chloride (1.36 mL, 15.6 mmol) was added dropwise to a cooled (0° C.) solution of the compound from Example 10 (2.15 g, 10.4 mmol) and dimethylformamide (1 drop) in tetrahydrofuran (40 mL). The mixture was warmed to room temperature for two hours then concentrated in vacuo to a volume of 20 mL. The solution was cooled to −78° C. and ammonia was condensed onto the mixture for two minutes. The mixture was warmed to room temperature for three hours, diluted with water (70 mL), and extracted with chloroform (3×70 mL). The combined organic phase was dried (MgSO$_4$), and concentrated to give a white solid (1.79 g, 84%). $^1$H NMR (300 MHz, CDCl$_3$) δ9.86 (s, 1H), 7.66 (m, 2H), 7.00 (d, J=8.5 Hz, 1H), 6.5 (br s, 1H), 5.7 (br s, 1H), 4.62 (dd, J=9.4 Hz, J=3.1 Hz, 1H), 2.89 (m, 2H), 2.46 (m, 1H), 2.11 (m, 1H); MS (EI) m/z 205 (M$^+$); R$_f$=0.2 (A).

EXAMPLE 12

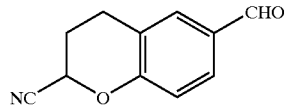

(±)-6-Formyl-chroman-2-carbonitrile

Trifluoroacetic anhydride (1.14 mL, 8.05 mmol) was added dropwise to a cooled (0° C.) solution of the compound from Example 11 (1.50 g, 7.32 mmol) and triethylamine (2.24 mL, 16.1 mmol) in tetrahydrofuran (10 mL). The mixture was warmed to room temperature. After 40 minutes the mixture was diluted with chloroform and washed with water, dilute aqueous hydrochloric acid, water, and saturated aqueous sodium chloride solution, dried (MgSO$_4$), and concentrated to afford an oil (1.30 g, 95%). $^1$H NMR (300 MHz, DMSO-d$_6$) δ9.86 (s, 1H), 7.72 (m, 2H), 7.07 (d, J=8.5 Hz, 1H), 5.65 (t, J=4.6 Hz, 1H), 2.94 (t, J=6.4 Hz, 2H), 2.28 (m, 2H); MS (CI) m/z 188 (MH$^+$); R$_f$=0.8 (B).

EXAMPLE 13

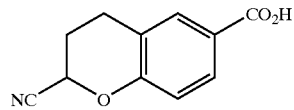

(±)-2-Cyano-chroman-6-carboxylic acid

A solution of sodium chlorite (1.18 g, 10.5 mmol, technical grade) in pH=3.5 buffer (7 mL×1.3 M) was added to a solution of the compound from Example 12 (1.30 g, 6.97 mmol) and 2-methyl-2-butene (7 mL) in 2-methyl-2-propanol (30 mL). After stirring overnight the mixture was brought to pH=10 with aqueous sodium hydroxide solution and the organics removed in vacuo. The aqueous phase was extracted with hexanes, brought to pH=3 with aqueous HCl solution, and extracted with chloroform then ethyl acetate. The organic phase was dried (MgSO$_4$) and concentrated to afford a white solid (1.21 g, 85%). $^1$H NMR (300 MHz, DMSO-d$_6$) δ12.7 (br s, 1H), 7.77 (d, J=1.8 Hz, 1H), 7.71 (dd, J=8.5 Hz, J=2.2 Hz, 1H), 6.95 (d, J=8.5 Hz, 1H), 5.61 (t, J=4.4 Hz, 1H), 2.90 (t, J=6.4 Hz, 2H), 2.25 (m, 2H); MS (EI) m/z 203 (M$^+$); R$_f$=0.2 (C).

EXAMPLE 14

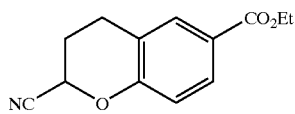

(±)-2-Cyano-chroman-6-carboxylic acid ethyl ester 1,8-Diazabicyclo[5.4.0]undec-7-ene (435 mL, 2.91 mmol) was added to a solution of the compound from Example 13 (591 mg, 2.91 mmol) in tetrahydrofuran (10 mL). After 10 minutes ethyl iodide (466 mL, 5.82 mmol) was added. After stirring overnight the mixture was diluted with water (25 mL) and extracted with diethyl ether (3×25 mL). The organic phase was washed with saturated aqueous sodium chloride solution, dried (MgSO$_4$), and concentrated. Silica gel chromatography (67:33 hexanes/ethyl acetate) afforded a colorless oil (523 mg, 78%). $^1$H NMR (300 MHz, DMSO-d$_6$) δ7.78 (d, J=1.8 Hz, 1H), 7.73 (dd, J=8.5 Hz, J=2.2 Hz, 1H), 6.98 (d, J=8.5 Hz, 1H), 5.62 (t, J=4.6 Hz, 1H), 4.27 (q, J=7.1 Hz, 2H), 2.91 (t, J=6.4 Hz, 2H), 2.25 (m, 2H), 1.29 (t, J=7.2 Hz, 3H); MS (EI) m/z 231 (M$^+$); R$_f$=0.7 (A).

EXAMPLE 15

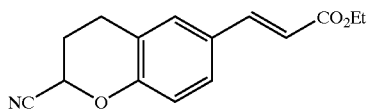

(±)-(E)-3-(2-Cyano-chroman-6-yl)-prop-2-enoic acid ethyl ester

A mixture of the compound from Example 12 (807 mg, 4.32 mmol) and (carbethoxymethylene)triphenylphosphorane (2.25 g, 6.47 mmol) in tetrahydrofuran (25 mL) was heated to reflux for 72 hours. The mixture was diluted with ethyl acetate, washed with saturated aqueous ammonium chloride solution, saturated aqueous sodium chloride solution, dried (MgSO$_4$), and concentrated. Silica gel chromatography (50:50 hexanes/ethyl acetate) afforded a white solid (953 mg, 86%). $^1$H NMR (300 MHz, DMSO-d$_6$) δ7.54 (m, 3H), 6.90 (d, J=8.5 Hz, 1H), 6.49 (d, J=16.2 Hz, 1H), 5.58 (t, J=4.6Hz, 1H), 4.16 (q, J=7.1 Hz, 2H), 2.85 (m, 2H), 2.23 (m, 2H), 1.24 (t, J=7.0 Hz, 3H). MS (Cl) m/z 258 (MH$^+$); R$_f$=0.7 (A).

EXAMPLE 16

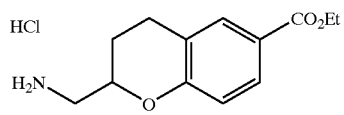

(±)-2-Aminomethyl-chroman-6-carboxylic acid ethyl ester hydrochloride

A mixture of the compound from Example 14 (570 mg, 2.47 mmol), concentrated HCL (2 mL) and 10% palladium on activated carbon (300 mg) in ethyl alcohol (120 mL) was placed under hydrogen pressure (45 psig) in a Parr hydrogenation apparatus. After 18.5 hours, the mixture was removed from the hydrogen atmosphere and filtered through a pad of Celite. The Celite pad was washed with ethyl alcohol (400 mL), and the combined filtrate concentrated to give a solid (670 mg, 100%). $^1$H NMR (300 MHz, DMSO-d$_6$) δ8.2 (br s, 2H), 7.70 (m, 2H), 6.89 (d, J=8.8 Hz, 1H), 4.35 (m, 1H), 4.25 (q, J=7.1 Hz, 2H), 3.18 (m, 1H), 3.08 (m, 1H), 2.84 (m, 2H), 2.08 (m, 1H), 1.71 (m, 1H), 1.28 (t, J=7.0 Hz, 3H); MS (EI) m/z 235 (M$^+$).

Examples 17 and 18 were Prepared in Analogy to the Procedure of Example 16

| Example | Name | MS |
| --- | --- | --- |
| 17 | (±)-3-(2-Aminomethyl-chroman-6-yl)-propionic acid ethyl ester hydrochloride | 264 (MH$^+$) |
| 18 | (±)-2-Aminomethyl-chroman-6-carboxylic acid hydrochloride | (Cl) 207 (MH$^+$) |

EXAMPLE 19

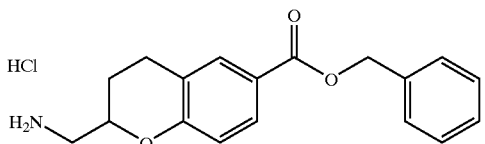

(±)-2-Aminomethyl-chroman-6-carboxylic acid benzyl ester hydrochloride

A solution of the compound from Example 18 (880 mg, 3.61 mmol) and sulfuric acid (0.75 mL) in benzyl alcohol (35 mL) was heated to 100° C. overnight. The mixture was diluted with diethyl ether, producing a white solid. The solid was collected by filtration, dissolved in ethyl acetate (80 mL), and washed with saturated NaHCO$_3$ (10 mL). The organic phase was concentrated in vacuo. The residue was dissolved in ethyl acetate (5 mL) and hydrogen chloride solution in diethyl ether added, producing a precipitate. The precipitate was collected by filtration to give a white solid (99 mg, 8%). $^1$H NMR (300 MHz, DMSO-d$_6$) δ8.30 (br s, 3H), 7.76 (m, 2H), 7.38 (m, 4H), 6.90 (d, J=8.8 Hz, 1H), 5.30 (s, 2H), 4.35 (m, 1H), 3.18 (m, 1H), 3.07 (m, 1H), 2.83 (m, 2H), 2.08 (m, 1H), 1.71 (m, 1H); MS (FAB) m/z 298 (MH$^+$); R$_f$ (free base)=0.3 (C).

EXAMPLE 20

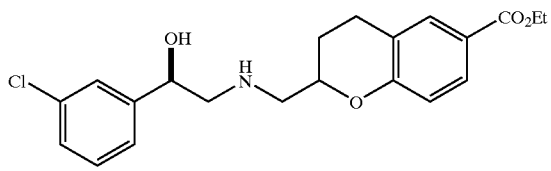

2-{[(2R)-2-(3-Chloro-phenyl)-2-hydroxy-
ethylamino]-methyl}chroman-6-carboxylic acid
ethyl ester A solution of the compound from Example 16 (50 mg, 185 mmol), (R)-(+)-3-chlorostyrene oxide (26 mg, 166 mmol), N,N-diisopropylethylamine (32 mL, 185 mmol), and lithium chloride in ethyl alcohol (5 mL) was heated to reflux for 60 hours. The reaction mixture was cooled to room temperature, filtered, and concentrated in vacuo. Silica gel chromatography (gradient elution from 67:33 hexanes/ethyl acetate to 50:50 hexanes/ethyl acetate to 45:45:10 hexanes/ethyl acetate/methanol) afforded a colorless oil (23 mg, 32%). $^1$H NMR (300 MHz, DMSO-$d_6$) δ7.69 (m, 2H), 7.32 (m, 4H), 6.82 (d, J=8.5 Hz, 1H), 5.47 (m, 1H), 4.65 (m, 1H), 4.24 (q, J=7.1 Hz, 2H), 4.16 (m, 1H), 2.9–2.6 (m, 5H), 2.01 (m, 1H), 1.67 (m, 1H), 1.28 (t, J=7.0 Hz, 3H); MS (FAB) m/z 390 (MH$^+$); $R_f$=0.3 (D).

Examples 21 and 22 were Prepared in Analogy to the Procedure of Example 20

| Example | Name | MS | TLC $R_f$ |
|---|---|---|---|
| 21 | 3-((2R)-2-{[2-(3-Chloro-phenyl)-2-hydroxy-ethylamino]-methyl}-chroman-6-yl)-propionic acid ethyl ester | 418 (MH$^+$) | 0.4 (D) |
| 22 | (2R)-2-{[2-hydroxy-2-pyridin-3-yl-ethylamino]-methyl}-chroman-6-carboxylic acid benzyl ester | 419 (MH$^+$) | 0.2 (E) |

EXAMPLE 23

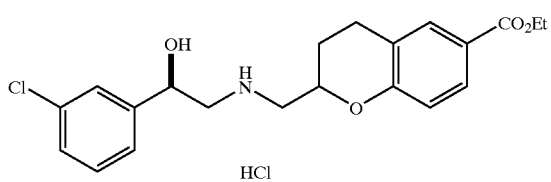

2{[(2R)-2-(3-Chloro-phenyl)-2-hydroxy-
ethylamino]-methyl}-chroman-6-carboxylic acid
ethyl ester hydrochloride Hydrogen chloride solution in diethyl ether (10 mL×1.0 M) was added to a solution of the compound from Example 20 in ethyl acetate (5 mL). The precipitate was collected by filtration and dried in vacuo to give a white solid (51 mg). Mp 234–235° C.; $^1$H NMR (300 MHz, DMSO-$d_6$) δ9.1 (br m, 2H), 7.74 (m, 2H), 7.41 (m, 4H), 6.91 (d, J=8.1 Hz, 1H), 6.35 (br s, 1H), 5.06 (m, 1H), 4.54 (m, 1H), 4.26 (q, J=7.1 Hz, 2H), 3.35 (m, 4H), 3.12 (m, 1H), 2.85 (m, 2H), 2.10 (m, 1H), 1.73 (m, 1H), 1.29 (t, J=7.0 Hz, 3H); MS (FAB) m/z 390 (MH$^+$).

EXAMPLE 24

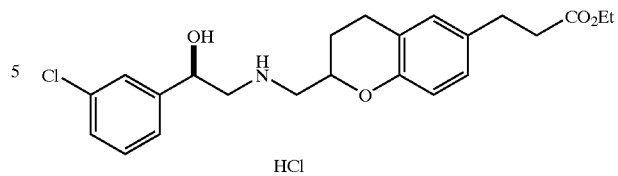

3-(2-{[(2R)-2-(3-Chloro-phenyl)-2-hydroxy-
ethylamino]-methyl}-chroman-6-yl)-propionic acid
ethyl ester hydrochloride The title compound was prepared in analogy to the procedure of Example 23. mp 189–190° C. MS (FAB) m/z 418 (MH$^+$).

EXAMPLE 25

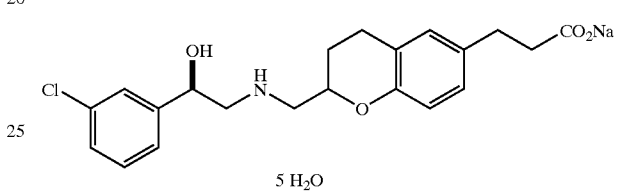

Sodium 3-(2-{[(2R)-2-(3-chloro-phenyl)-2-hydroxy-
ethylamino]-methyl}-chroman-6-yl)-propionate
pentahydrate A solution of the product from Example 20 (110 mg, 263 mmol) and sodium hydroxide (180 mg, 4.5 mmol) in methanol (10 mL) was heated to reflux overnight. The methanol was removed by azeotropic distillation with water. HPLC (C18 reversed phase silica gel) afforded a white solid (15 mg, 11%). $^1$H NMR (300 MHz, DMSO-$d_6$) δ7.32 (m, 4H), 6.83 (m, 2H), 6.55 (m, 1H), 5.52 (m, 1H), 4.66 (m, 1H), 3.98 (m, 1H), 2.8–2.55 (m, 7H), 2.04 (m, 2H), 1.92 (m, 1H), 1.61 (m, 1H); MS (FAB) m/z 390 (MH$^+$ of protonated carboxylate).

EXAMPLE 26

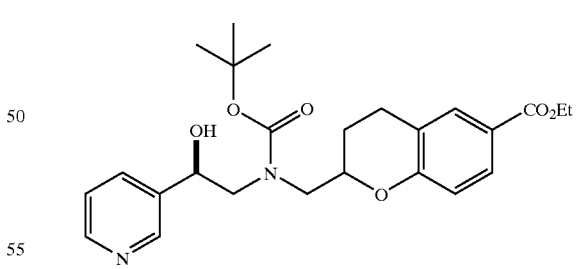

2-{[tert-Butoxycarbonyl-((2R)-2-hydroxy-2-pyridin-
3-yl-ethyl)-amino]-methyl}-chroman-6-carboxylic
acid ethyl ester A mixture of the compound from Example 16 (217 mg, 800 mmol), (R)-pyrid-3-yloxirane (88 mg, 730 mmol, triethylamine (125 mL), and lithium in 88:12 ethanol/water (17 mL) was heated to reflux for five days. The mixture was concentrated in vacuo. The residue was dissolved in tetrahydrofuran (5 mL) and cooled to 0° C. A solution of di-tertbutyl dicarbonate (276 mL, 1.20 mmol) in tetrahydrofuran (1 mL) was added and the cold bath was removed. After two hours methanol was added. Silica gel chromatography (gradient elution from 67:33 hexane/ethyl acetate to ethyl acetate) afforded a colorless oil (58 mg, 16%). $R_f$=0.2 (C).

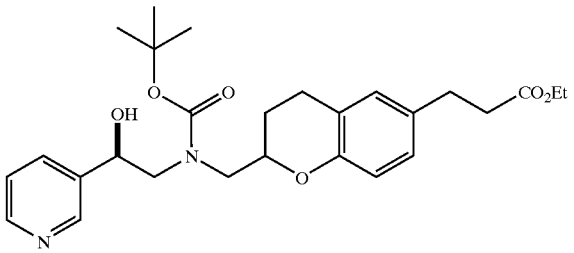

EXAMPLE 27

3-((2R)-2-{[tert-Butoxycarbonyl-(2-hydroxy-2-pyridin-3-yl-ethyl)-amino]-methyl}-chroman-6-yl)-propionic acid ethyl ester The title compound was prepared in analogy to the procedure of Example 26. MS (FAB) m/z 485 (MH+). $R_f$=0.4 (D).

EXAMPLE 28

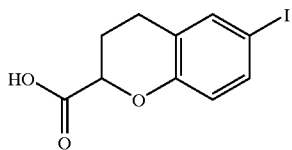

6-Iodochromane-2-carboxylic acid

A mixture of the compound from Example 20 (5.00 g, 28.1 mmol) and zinc chloride (ca 5 g) were placed in a round bottom flask. Glacial acetic acid (150 mL) was added followed by benzyltrimethylammonium dichloroiodate (9.65 g, 28.1 mmol). The resulting orange mixture was stirred at room temperature for 18 h and then poured into water (300 mL). The resulting mixture was extracted with dichloromethane (3×). The combined organic phases were dried (MgSO4) and concentrated to an oily residue. The residue was mixed with water (150 mL) to produce a white suspension. The suspended solids were collected by filtration, washed with water (2×), and dried to yield a white solid (7.14 g, 84%). $^H{}^1$ NMR (300 MHz, acetone-$d_6$) δ11.33 (s, 1H), 7.39 (m, 2H), 6.65 (m, 1H), 4.83 (m, 1H), 2.78 (m, 2H), 2.18 (m, 2H). MS (EI) m/z 304 (M+).

EXAMPLE 29

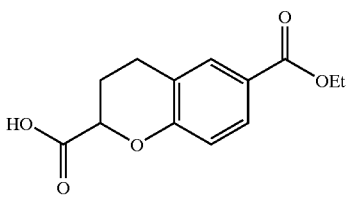

6-(Ethoxycarbonyl)chromane-2-carboxylic acid

A 2-neck round bottom flask fit with a reflux condenser was charged the compound from Example 28 (1.05 g, 3.45 mmol) and palladium (II) acetate (23 mg, 0.10 mmol). The flask was placed under an atmosphere of carbon monoxide (1 atm). Triethylamine (1.20 mL, 8.63 mmol) and absolute ethanol (2.0 mL) were added via syringe. The dark reaction mixture was heated to 60° C. and stirred for 60 h. The reaction mixture was cooled to room temperature and diluted with ethyl acetate (100 mL). The resulting dark solution was washed sequentially with 7% aqueous hydrochloric acid, water, and saturated aquesous sodium chloride. The organic layer was dried (MgSO$_4$), and concentrated to an orange oil which crystallized on standing to a pale solid (0.675 g, 81%). $^1$H NMR (300 MHz, DMSO-$d_6$) δ13.03 (s, 1H), 7.68 (m, 2H), 6.90 (m, 1H), 4.89 (m, 1H), 4.25 (q, J=7.36 Hz, 2H), 2.82 (m, 1H), 2.66 (m, 1H), 1.28 (t, J=6.98 Hz, 3H); MS (CI) m/z 251 (MH+).

EXAMPLE 30

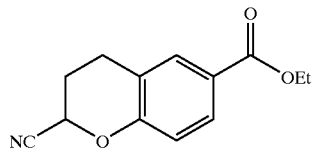

(±)-2-Cyano-chroman-6-carboxylic acid ethyl ester

In a round bottom flask under an argon atmosphere, a mixture of the compound from Example 29 (0.600 g, 2.40 mmol) and N,N-dimethylformamide (1 drop) were stirred in tetrahydrofuran (15 mL). The clear solution was stirred at room temperature and oxalyl chloride (0.314 mL, 3.60 mmol) was added via syringe. The mixture was stirred for 2 h and then concentrated to approximately 50% of its original volume. The resulting solution was cooled to 0° C. A 0.5 M solution of ammonia in 1,4-dioxane (10 mL, 5.0 mmol) was added via syringe and the resulting mixture stirred for 1 h at 0° C. The reaction mixture was then poured into ice water (40 mL) and the resulting suspension extracted with chloroform (3×). The combined organic layers were washed with saturated aqueous sodium chloride, dried (MgSO$_4$), and concentrated to an orange solid. The orange solid was dissolved in tetrahydrofuran (5 mL) and triethylamine (0.735 mL, 5.28 mmol) and cooled to 0° C. under an argon atmosphere. Trifluoroacetic anhydride (0.373 mL, 2.64 mmol) was added dropwise via syringe to produce a purple solution. Following the addition, the reaction was poured into acidic water and the resulting mixture extracted with ethyl acetate (2×). The combined organic layers were washed with saturated aqueous sodium chloride, dried (MgSO$_4$), and concentrated to a purple oil. Silica gel chromatography (50:50 hexanes/ethyl acetate) afforded an orange oil (0.232 g, 42%). The analytical data are the same as Example 14.

EXAMPLE 31

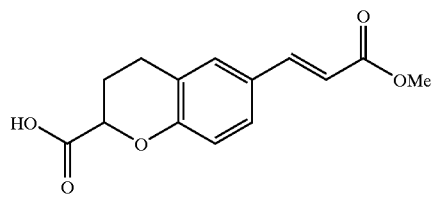

6-[(1E)-2-(Methoxycarbonyl)vinyl]chromane-2-carboxylic acid

Palladium (II) acetate (0.15 g, 0.66 mmol) and the compound from Example 28 (2.00 g, 6.58 mmol) were put in a round bottom flask under an argon atmosphere. To the flask was added 1-methyl-2-pyrrolidinone (20 mL), methyl acrylate (0.74 mL, 8.22 mmol), and triethylamine (2.29 mL, 16.5 mmol). The mixture was heated to 70° C. and stirred for 400 h. The reaction was cooled to RT and poured into water (70 mL). The mixture was extracted with ethyl acetate (1×). The aqueous layer was then acidified with 1.0 N aqueous HCl to generate a cloudy mixture. The mixture was extracted with ethyl acetate (3×). The combined organics from the second extraction were dried ($MgSO_4$) and concentrated to a tan solid (1.75 g, 100%). $^1$H NMR (300 MHz, acetone-$d_6$) δ11.28 (s, 1H), 7.57 (d, J=16.18 Hz, 1H), 7.43 (m, 1H), 7.40 (m, 1H), 6.86 (m, 1H), 6.37 (d, J=16.18 Hz, 1H), 4.88 (m, 1H), 3.70 (s, 3H), 2.85 (m, 2H), 2.24 (m, 2H); MS (ES) m/z 263 (MH+).

EXAMPLE 32

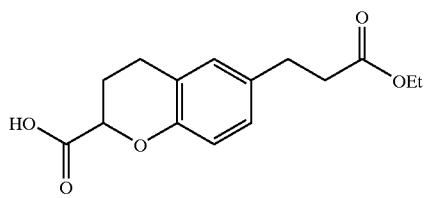

6-[2-(ethoxycarbonyl)ethyl]chromane-2-carboxylic acid

In a round bottom flask the compound from Example 31 (0.455 g, 1.74 mmol) was stirred in anhydrous methanol (10 mL) under an argon atmosphere. Copper (I) chloride (0.26 g, 2.6 mmol) was added and the mixture was cooled to 0° C. Sodium borohydride (0.457 g, 17.4 mmol) was added in four portions over 40 minutes. Gas evolution was observed with each addition. The resulting black mixture was stirred for 15 min and then poured into 100 mL water. The aqueous mixture was made acidic by addition of 1.0 N aqueous HCl and extracted with ethyl acetate (3×). The combined organic layers were dried ($MgSO_4$), filtered through celite, and concentrated to a white solid (0.412 g, 90%). $^1$H NMR (300 MHz, acetone-$d_6$) δ11.18 (s, 1H), 6.90 (m, 2H), 6.72 (m, 1H), 4.74 (m, 1H), 3.57 (s, 3H), 2.77 (m, 4H), 2.55 (m, 2H), 2.17 (m, 2H).

EXAMPLE 33

A capsule formula is prepared from

| 2-{[(2R)-2-(3-chloro-phenyl)-2-hydoxy-ethylamino]-methyl}-chroman-6-carboxylic acid ethyl ester | 40 mg |
|---|---|
| Starch | 109 mg |
| Magnesium steatrate | 1 mg |

The components are blended, passed through an appropriate mesh sieve, and filled into hard gelatin capsules.

EXAMPLE 34

A tablet is prepared from

| (2-{[2-(6-Amino-pyridin-3-yl)-2-hydroxy-ethylamino]-methyl}-chroman-6-yl)-acetic acid | 25 mg |
|---|---|
| Cellulose, microcrystaline | 200 mg |
| Colloidal silicon dioxide | 10 mg |
| Stearic acid | 5.0 mg |

The ingredients are mixed and compressed to form tablets.

It should be apparent to one of ordinary skill in the art that changes and modifications can be made to this invention without departing from the spirit or scope of the invention as it is set forth herein.

What is claimed as new and useful is:

1. A compound of the formula:

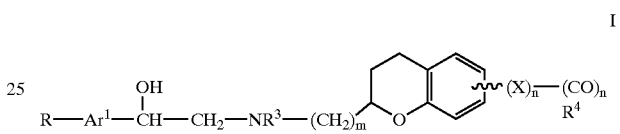

wherein:

R is hydrogen, hydroxy, oxo, halogen, $C_1$–$C_{10}$haloalkyl, $C_1$–$C_{10}$ alkyl, cyano, nitro, $NR^1R^1$, $SR^1$, $OR^1$, $SO_2R^2$, $OCOR^2$, $NR^1COR^2$, $COR^2$, $NR^1SO_2R^2$, $NR^1CO_2R^1$, phenyl;

$R^1$ is hydrogen, $C_1$–$C_{10}$ alkyl optionally substituted with 1 to 4 substituents selected from hydroxy, halogen, $CO_2H$, $CO_2C_1$–$C_{10}$ alkyl, $SO_2C_1$–$C_{10}$ alkyl, $C_1$–$C_{10}$ alkoxy; or $C_3$–$C_8$ cycloalkyl, phenyl or naphthyl each optionally substituted with 1 to 4 substituents selected from halogen, nitro, oxo, $C_1$–$C_{10}$ alkyl, $C_1$–$C_{10}$ alkoxy, and $C_1$–$C_{10}$ alkylthio;

$R^2$ is $R^1$ or $NR^1R^1$;

$R^3$ is hydrogen, $C_1$–$C_{10}$ alkyl, $CO_2R^1$, or

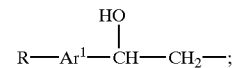

$Ar^1$ is pyridyl;

m is 1, 2, or 3;

n is independently in each instance 0, 1, or 2;

X is $C_1$–$C_4$ alkyl optionally substituted with halogen;

$R^4$ is O—$R^1$ or $NR^1R^1$, or a pharmaceutically acceptable salt or ester thereof.

2. A compound of claim 1 wherein $R^3$ is hydrogen and m is one.

3. A compound of claim 2 wherein $(X)_n$—$(CO)_n R^4$ is attached to the chroman moiety in the 6 position, $(X)_n$ is $C_1$–$C_4$ alkyl, and $(CO)_n R^4$ is $CO_2R^1$.

4. A compound of claim 1 wherein the —OH group of the compound of Formula 1 is in the Rectus configuration.

5. A pharmaceutical composition comprising an effective amount of a compound of claim 1 in combination with a pharmaceutically acceptable carrier.

6. A composition comprising an effective amount of a compound of claim 1, in combination with an inert carrier.

7. A method of treating obesity in mammals which comprises administering to a mammal in need thereof a pharmaceutically effective amount of a compound of claim 1.

8. A method of treating obesity in mammals which comprises administering to a mammal in need thereof a pharmaceutically effective amount of a composition of claim 5.

9. A method of treating diabetes in mammals which comprises administering to a mammal in need thereof a pharmaceutically effective amount of a compound of claim 1.

10. A method of treating diabetes in mammals which comprises administering to a mammal in need thereof a pharmaceutically effective amount of a composition of claim 5.

11. A method of using a compound of claim 1 for producing a beta-3 adrenergic receptor agonistic effect in a patient in need thereof comprising administering to said patient a pharmaceutically effective amount of a compound of claim 1.

* * * * *